(12) United States Patent
Matsumoto et al.

(10) Patent No.: US 8,506,785 B2
(45) Date of Patent: Aug. 13, 2013

(54) ANALYSIS APPARATUS WITH RENEWABLE ELECTRODE CONTACT TIP

(75) Inventors: Daisuke Matsumoto, Kyoto (JP); Yasunori Shiraki, Kyoto (JP); Yusuke Nakayama, Kyoto (JP); Genki Adachi, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 171 days.

(21) Appl. No.: 13/196,578

(22) Filed: Aug. 2, 2011

(65) Prior Publication Data

US 2012/0031761 A1 Feb. 9, 2012

(30) Foreign Application Priority Data

Aug. 3, 2010 (JP) ................................. 2010-174133

(51) Int. Cl.
*G01N 27/453* (2006.01)
(52) U.S. Cl.
USPC .......................................... 204/650; 204/601

(58) Field of Classification Search
USPC ......................................... 204/600–605, 650
See application file for complete search history.

(56) References Cited

U.S. PATENT DOCUMENTS

2001/0005489 A1* 6/2001 Roach et al. .................... 422/99

FOREIGN PATENT DOCUMENTS

JP 2009-145245 A 7/2009

* cited by examiner

*Primary Examiner* — J. Christopher Ball
(74) *Attorney, Agent, or Firm* — Fox Rothschild LLP

(57) ABSTRACT

An analysis apparatus enables a plurality of analysis processes to be accurately and efficiently performed. The analysis apparatus includes a detention tank in which a specimen is stored, and a voltage applier. The voltage applier includes a power source and a contact tip to be brought into contact with the specimen for applying a voltage necessary for analyzing the specimen. The voltage applier renews the contact tip from a used state to an unused state after completing an analysis and before starting the subsequent analysis.

17 Claims, 13 Drawing Sheets

ANALYSIS APPARATUS WITH RENEWABLE ELECTRODE CONTACT TIP

INCORPORATION BY REFERENCE

The present application claims priority under 35 U.S.C. §119 to Japanese Patent Application No. 2010-174133 filed on Aug. 3, 2010, the content of which is incorporated herein by reference in its entirety.

BACKGROUND OF THE INVENTION

1. Field of the Invention

The present invention relates to an analysis apparatus utilizing an electrophoresis process, for example.

2. Description of Related Art

To analyze a specimen for quantitating the concentration or amount of a specific component contained, an analysis method based on a capillary electrophoresis process is widely employed. In the capillary electrophoresis process, an electrophoretic liquid is loaded in a separation channel having a relatively small cross-sectional area, and the specimen is introduced into the separation channel from an end portion thereof. Then upon applying a voltage to both ends of the separation channel, the electrophoretic liquid flows from the anode toward the cathode, thereby generating an electroosmotic flow. At the same time, the specific component of the specimen is driven to move in accordance with its electrophoretic mobility, by the applied voltage. Accordingly, the specific component migrates as expressed by a velocity vector generated by merging the velocity vector of the electroosmotic flow and the velocity vector of the electrophoretic movement. As a result, the specific component is separated from other components of the specimen. Then the amount and concentration of the specific component can be analyzed by detecting, for example by an optical method, the specific component thus separated.

FIG. 13 depicts a conventional analysis apparatus. The analysis apparatus X shown therein includes a microchip 91 and a voltage applier 92. An introduction tank 911, a drain tank 913, and a separation channel 912 communicating between these tanks are provided on the microchip 91. An electrophoretic liquid is loaded in the introduction tank 911 and the separation channel 912 in preparation for the analysis. A specimen S, the object of the analysis such as blood, is stored in a specimen container B. The specimen S is introduced into the introduction tank 911 through an introduction nozzle 93. The voltage applier 92 includes a power source 921 and electrodes 922, 923. To perform the analysis, the electrode 922 is soaked in the introduction tank 911 and the electrode 923 is soaked in the drain tank 913. Upon applying a predetermined voltage between the electrodes 922, 923, a specific component of the specimen S starts to be separated by electrophoresis. A light emitter 941 and a light receptor 942 are disposed halfway of the separation channel 912, so as to oppose each other across the separation channel 912. To the light emitter 941, a light source 943 supplies a light. The light receptor 942 is connected to a detector 944. Thus, the concentration of the specific component of the specimen S can be measured by measuring for example the absorbance of the specimen S by the detector 944.

However, once an analysis process is performed, the specimen S sticks to the electrode 922. Also, as a result of applying a voltage for the electrophoresis, the components of the specimen S and electrophoretic liquid are deposited on the electrode 922. Utilizing again the electrode 922 under such a condition for subsequent analysis processes may allow different specimens to be mixed, or allow the deposited components to be mixed in the specimen for the subsequent analysis processes. To prevent such situations, the operator has to assume a burden of manually replacing the electrode 922 prior to each analysis process, which makes the operation inconvenient and inefficient.

SUMMARY OF THE INVENTION

The present invention has been proposed under the foregoing situation, and provides an analysis apparatus that enables a plurality of analysis processes to be accurately and efficiently performed.

The analysis apparatus according to the present invention includes a detention tank in which a liquid is stored, a voltage applier including a power source and a contact tip to be brought into contact with the liquid for applying a voltage necessary for analyzing the liquid. The voltage applier renews the contact tip from a used state to an unused state after completing an analysis and before starting a subsequent analysis.

Preferably, the voltage applier may include a plurality of electrodes to be sequentially soaked in the detention tank, and utilize the electrode soaked in the liquid as the contact tip.

Preferably, the voltage applier may further include a retention unit that retains the plurality of electrodes aligned thereon, so as to form a circle concentric with a center of the retention unit, about which the retention unit is configured to rotate.

Preferably, the retention unit may include a conductive portion for electrical connection between the power source and each of the electrodes.

Preferably, each of the electrodes may have a bar shape, and may be disposed such that a longitudinal axis thereof is parallel to a rotary shaft of the retention unit.

Preferably, each of the electrodes may have a bar shape, and may be disposed such that a longitudinal axis thereof is oriented in a radial direction of the retention unit perpendicular to the rotary shaft.

Preferably, each of the electrodes may include a through-hole longitudinally penetrating therethrough, and the voltage applier may further include an introduction nozzle for introducing the liquid through the through-hole.

Preferably, the introduction nozzle may be configured to cause each of the electrodes to move toward the detention tank.

Preferably, the voltage applier may further include a cleaning mechanism that cleans one of the electrodes that is not in use as the contact tip.

Preferably, the cleaning mechanism may be configured to inject and discharge a cleaning liquid to and from the electrode to be cleaned.

Preferably, the cleaning mechanism may apply a voltage to the electrode to be cleaned.

Preferably, each of the plurality of electrodes may have a bar shape, and the voltage applier may further include a retention unit that slidably retains the plurality of electrode serially aligned in a longitudinal direction thereof.

Preferably, the retention unit may include a conductive portion for electrical connection between the power source and each of the electrodes.

Preferably, each of the electrodes may include a through-hole longitudinally penetrating therethrough, and the voltage applier may further include an introduction nozzle for introducing the liquid through the through-hole.

Preferably, the voltage applier may include a bar-shaped electrode, and a cutter that cuts the electrode so as to longitudinally divide the electrode.

Preferably, the electrode may include a plurality of narrowed portions located at intervals and smaller in cross-sectional area orthogonal to the longitudinal direction, and the cutter may cut the electrode at the narrowed portion.

Preferably, the voltage applier may include a tape-shaped electrode, a delivery wheel that delivers the electrode wound thereon, and a takeup wheel that takes up the electrode delivered from the delivery wheel, and may use a portion of the electrode soaked in the liquid as the contact tip.

Preferably, the voltage applier may further include a sticking bar that causes a portion of the electrode located between the delivery wheel and the takeup wheel to detour through the detention tank.

Preferably, the sticking bar may be formed of a conductive material and connected to the power source.

Preferably, the analysis may be preformed utilizing an electrophoresis process.

Preferably, the detention tank may receive a specimen to be subjected to the analysis.

The analysis apparatus thus configured allows a contact tip of an unused state to be utilized for each of the analysis processes. Accordingly, the specimen stuck to the contact tip and components of the electrophoretic liquid deposited thereon during an analysis process can be prevented from being mixed in an electrophoretic liquid or specimen to be subjected to a subsequent analysis process. The foregoing analysis apparatus allows, therefore, analysis processes of a plurality of specimens to be accurately and efficiently performed.

The above and other features and advantages of the present invention will become more apparent through detailed description given hereunder referring to the accompanying drawings.

DETAILED DESCRIPTION OF THE PREFERRED EMBODIMENTS

Preferred embodiments of the present invention will be described below in details referring to the accompanying drawings.

Figure 1:
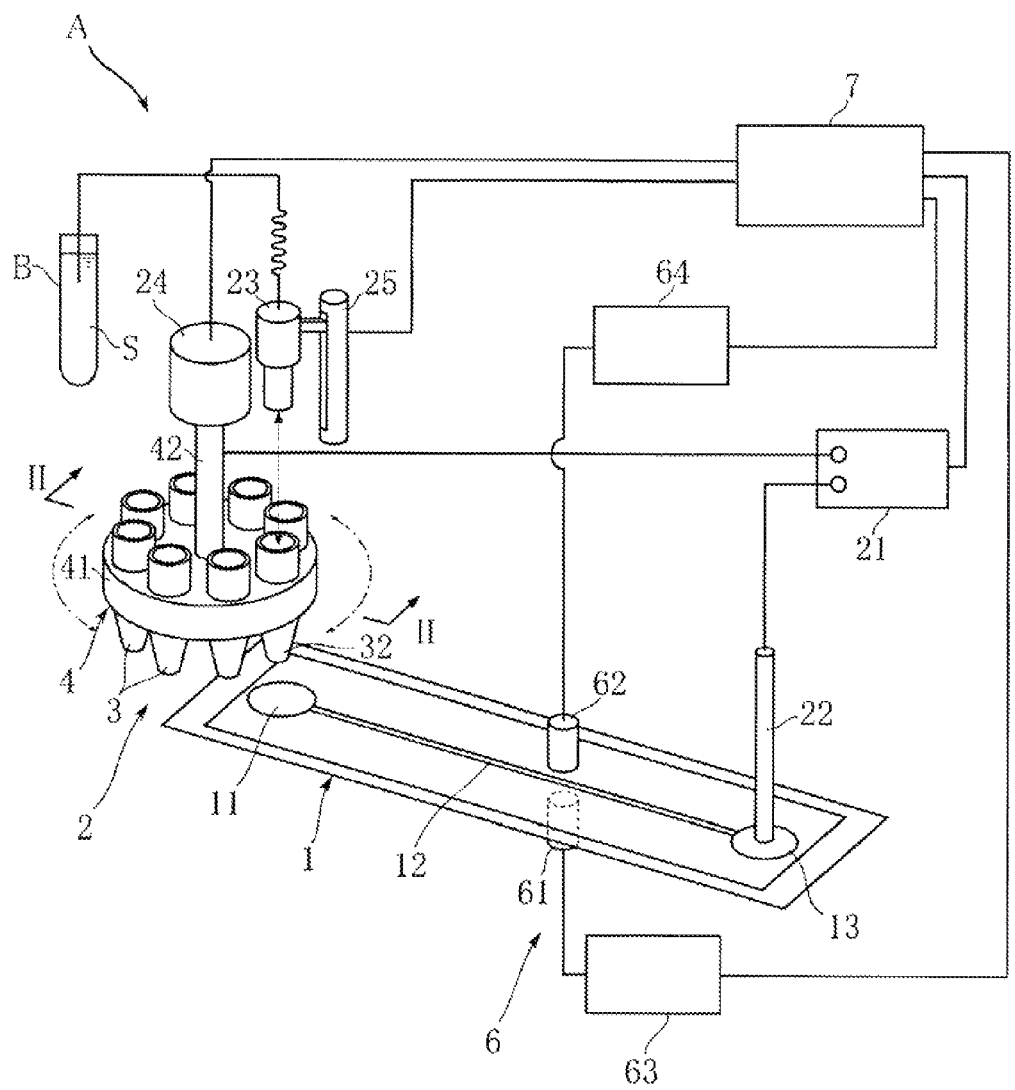
FIG. 1 is a schematic diagram showing an overall configuration of an analysis apparatus according to the present invention.

FIG. 1 depicts an example of an analysis apparatus according to the present invention. The analysis apparatus A according to this embodiment includes a microchip 1, a voltage applier 2, an analyzer 6, and a control unit 7. In this embodiment, the analysis apparatus A employs a capillary electrophoresis process for the analysis.

The microchip 1 is formed of silica for example, and includes an introduction tank 11, a separation channel 12, and a drain tank 13. The introduction tank 11, which exemplifies a detention tank according to the present invention, serves to receive an electrophoretic liquid Lq that acts as a buffer in the capillary electrophoresis process, and a specimen S to be analyzed. The electrophoretic liquid Lq may contain, for example, a 100 mM malic acid-arginine buffer (pH 5.0) and 1.5 chondroitin sulfate C sodium salt. The specimen S may be exemplified by blood, although the present invention is not limited thereto. A liquid other than blood, such as sweat, saliva, or urine may be employed as the specimen S.

The separation channel 12 is the actual site where the capillary electrophoresis process is performed, and generally formed as a microchannel. Preferably, the separation channel 12 may have a length of approx. 30 mm, and a circular cross-section of 25 to 100 μm in diameter or a rectangular cross-section of 25 to 100 μm in side length, as an example.

The drain tank 13 is located on a downstream side of the separation channel 12 with respect to the flow direction of the capillary electrophoresis process. A drain nozzle (not shown) is attached to the drain tank 13. The drain nozzle serves to discharge the specimen S and the electrophoretic liquid Lq that have undergone the analysis with a suction pump (not shown).

The voltage applier 2 serves to apply a voltage required for the capillary electrophoresis process to the respective ends of the separation channel 12 through the introduction tank 11 and the drain tank 12, and includes a power source 21, a plurality of electrodes 3, a retention unit 4, a drain-side electrode 22, an introduction nozzle 23, a motor 24, and an actuator 25.

The power source 21 generates the voltage required for the capillary electrophoresis process, for example 1.5 kV. The drain-side electrode 22 is formed of Cu for example, and connected to a terminal of the power source 21 to be soaked in the drain tank 13.

Figure 2:
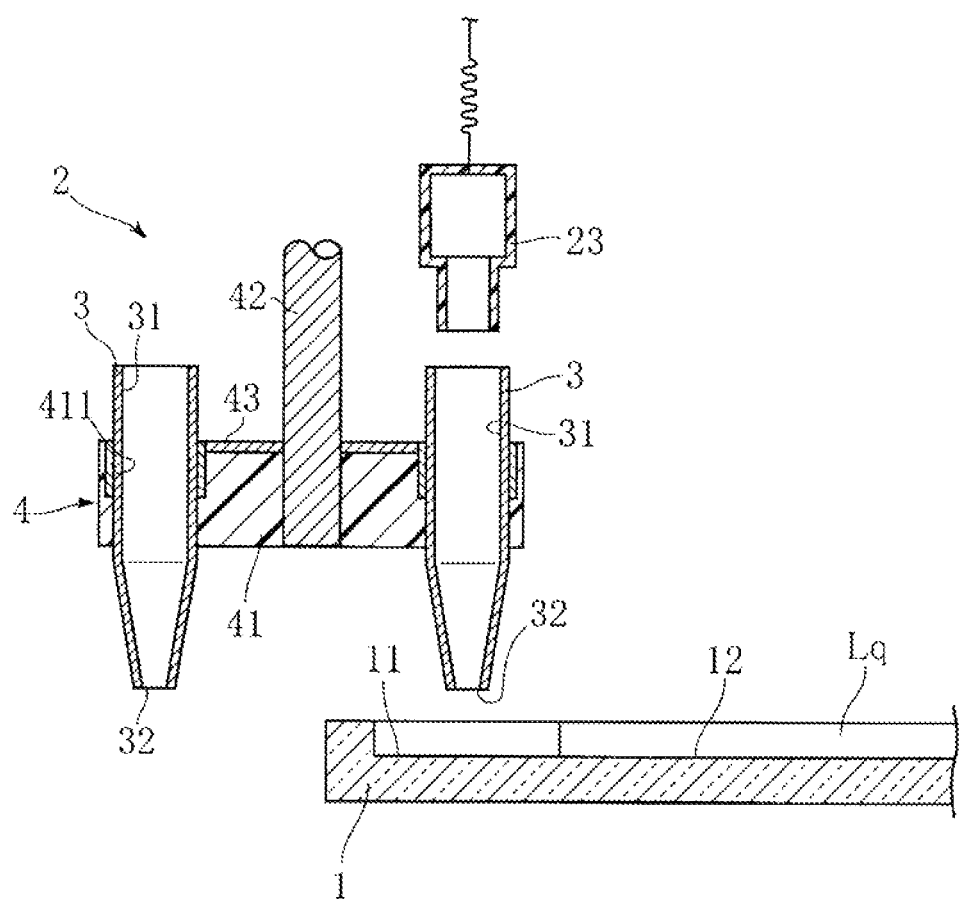
FIG. 2 is a fragmentary cross-sectional view taken along a line II-II in FIG. 1.

The plurality of electrodes 3 is also formed of Cu, for example, and set to be soaked in the introduction tank 11. As shown in FIG. 2, the electrodes 3 each include a through-hole 31. Accordingly, the electrodes 3 serve as a dispenser nozzle for dispensing the specimen S, as will be subsequently described. In this embodiment, each electrode 3 has a generally cylindrical shape with a tapered tip portion oriented downward.

The retention unit 4, which serves to retain the plurality of electrodes 3, includes a main body 41, a rotary shaft 42, and a conductive portion 43. The main body 41 is formed, for example, of a resin material in a thick disk shape. The rotary shaft 42 is attached to a central portion of the main body 41. In this embodiment, the rotary shaft 42 is either entirely formed of a conductive material such as Cu or includes a conductive portion, and is connected to a terminal of the power source 21. As shown in FIG. 1, a motor 24 is connected to an upper end portion of the rotary shaft 42. The motor 24 may be a servo motor for example, and is capable of rotating the retention unit 4 by a desired angle.

The main body 41 includes a plurality of retention orifices 411. In this embodiment, the main body 41 includes eight retention orifices 411. The retention orifices 411 are aligned on the main body 41 about the rotary shaft 24 so as to form a concentric circle with the main body 41. The retention orifices 411 are each formed so as to penetrate through the main body 41 parallel to the rotary shaft 24, and slidably retains the respective electrode 3. Thus, in this embodiment, eight electrodes 3 are circumferentially located about the rotary shaft 24, parallel to each other. The conductive portion 43 is formed of Cu for example, and disposed in contact with the rotary shaft 24 and exposed on the inner surface of each retention orifice 411. Accordingly, the plurality of electrodes 3 is electrically connected to the terminal of the power source 21 through the rotary shaft 24 and the conductive portion 43.

The introduction nozzle 23 serves to introduce the specimen S through the electrode 3, and is connected to a specimen container B in which the specimen S is stored, through a hose or the like as shown in FIG. 1. In this embodiment, the outer diameter of a lower portion of the introduction nozzle 23 is slightly smaller than the inner diameter of the through-hole 31 of the electrode 3. In the case where the blood, an example of the specimen S, has to be diluted to a predetermined concentration, a specimen diluter (not shown) is connected to the introduction nozzle 23. The actuator 25 is a driver that serves to move the introduction nozzle 23 up and downward.

The analyzer 6 executes, for example, measurement of absorbance, and includes a light emitter 61, a light receptor 62, a light source 63, and a detector 64 as shown in FIG. 1. The light source 63 generates a light beam to be used for the measurement of absorbance, and includes a laser element (not shown) for example. In the case of analyzing, for example, concentration of hemoglobin A1c, the light source 63 may generate a light beam of a wavelength of 415 nm. The light emitter 61 is connected to the light source 63 for example through, an optical fiber, and emits the light beam from the light source 63 to a part of the separation channel 12. The light receptor 62 receives the light from the separation channel 12, and is connected to the detector 64 for example through an optical fiber. The detector 64 detects the light received by the light receptor 62.

The control unit 7 serves to control the operation of the components of the analysis apparatus A, and executes a series of controlling actions for the analysis apparatus A to perform an analysis. The control unit 7 includes a CPU, a memory, an I/O interface, or the like.

Hereunder, an analyzing operation of the analysis apparatus A will be described.

Figure 3:
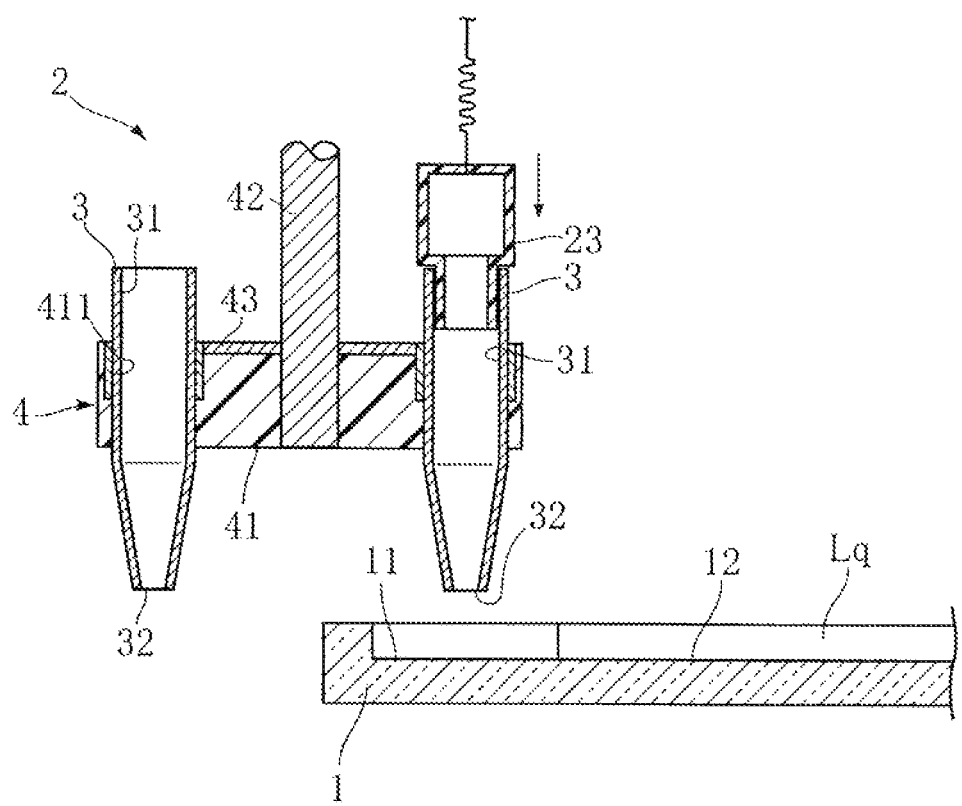
FIG. 3 is a fragmentary cross-sectional view showing a state where an introduction nozzle has moved forward.

First, the electrophoretic liquid Lq acting as a buffer is loaded in the introduction tank 11 and the separation channel 12 of the microchip 1, as shown in FIG. 2. One of the plurality of electrodes 3 is located right above the introduction tank 11. Then the actuator 25 causes, in accordance with an instruction from the control unit 7, the introduction nozzle 23 to descend toward the electrode 3 located right above the introduction tank 11, as shown in FIG. 3. Accordingly, the lower portion of the introduction nozzle 23 intrudes into the through-hole 31 of the electrode 3. As a result, the introduction nozzle 23 and the electrode 3 are unified.

Figure 4:
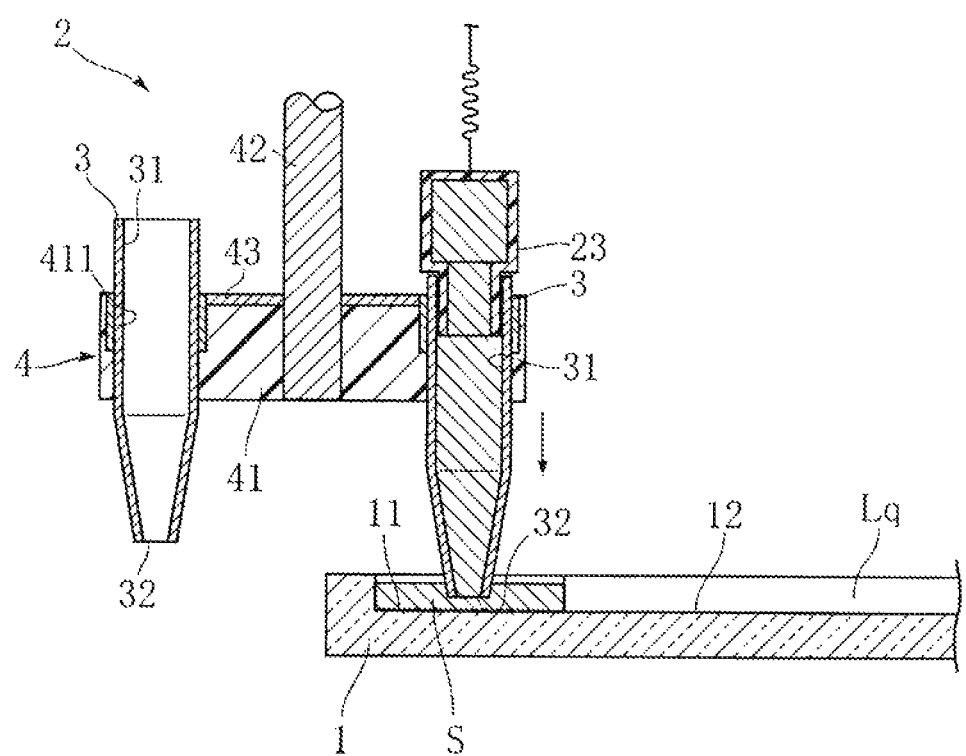
FIG. 4 is a fragmentary cross-sectional view showing a state where a specimen is being introduced.

Referring to FIG. 4, as the actuator 25 moves the introduction nozzle 23 further downward, the lower end portion of the electrode 3 is soaked in the electrophoretic liquid Lq in the introduction tank 11. The portion soaked in the electrophoretic liquid Lq serves as the contact tip 32. Then a pump (not shown) dispenses a predetermined amount of specimen S into the introduction tank 11 through the introduction nozzle 23 and the electrode 3. Thus, the electrode 3 serves also as a dispenser nozzle for dispensing the specimen S. As a result, the contact tip 32 of the electrode 3 is soaked in the specimen S dispensed into the introduction tank 11. Then the control unit 7 activates the power source 21 to apply a voltage through the electrode 3 and the drain-side electrode 22. This generates electrophoresis in the separation channel 12. The electrophoresis causes, for example, the hemoglobin A1c to migrate along the separation channel 12. Then the analyzer 6 measures the absorbance to thereby analyze the hemoglobin (A1c) concentration of the specimen S.

Upon completing the foregoing analysis process, the control unit 7 instructs the actuator 25 to cause the introduction nozzle 23 to ascend. Together with the introduction nozzle 23, the electrode 3 is made to ascend. Such an ascending actions may be performed, for example, by a spring (not shown) provided in the retention unit 4 for exerting an elastic force that biases the electrode 3 to ascend, from the state shown in FIG. 4 to the state shown in FIG. 2. Alternatively, another actuator (not shown) that causes the electrode 3 to ascend may be provided. Now, in preparation for the next analysis process, the control unit 7 instructs the motor 24 to rotate the retention unit 4 by a predetermined angle (45 degrees in this embodiment). Accordingly, the electrode 3 located adjacent to the one used for the preceding analysis process is brought to the position right above the introduction tank 11. At this stage, the contact tip 32 is renewed from a used state to an unused state. After the renewal of the contact tip 32, the same analysis operation is repeated. Thus, a plurality of different specimens S can be successively analyzed by repeating the foregoing analysis operation and the renewal of the contact tip 32.

Advantageous effects of the analysis apparatus A will now be described.

The analysis apparatus A according to this embodiment allows a renewed one of the electrodes 3 for each analysis process. Accordingly, the specimen S stuck to the contact tip 32 and components of the electrophoretic liquid Lq deposited thereon during an analysis process can be prevented from being mixed in the electrophoretic liquid Lq or specimen S to be subjected to a subsequent analysis process. The analysis apparatus A allows, therefore, analysis of a plurality of specimens to be accurately and efficiently performed. Also, the electrodes 3 can be automatically replaced by causing the motor 24 to rotate the retention unit under the control of the control unit 7. Such an arrangement allows the plurality of analysis processes to be efficiently performed in a shorter time, for example compared with the case where the operator manually replaces the electrodes 3.

Locating the plurality of electrodes 3 on the retention unit 4 concentrically therewith allows an unused one of the electrodes 3 to be brought to a working position simply by rotating the retention unit 4, which improves the convenience of use. Providing the conductive portion 43 on the retention unit 4 allows the respective electrodes 3 and the power source 21 to be electrically connected upon placing the electrodes 3 on the retention unit 4.

As stated above, the electrode 3 serves also as the dispenser nozzle. Accordingly, the specimen S can be quickly dispensed upon bringing the electrode 3 to the position for applying a voltage. This advantageous for shortening the time required for the analysis. Making the electrode 3 descend utilizing the introduction nozzle 23 provides the advantage in that a single action allows both application of a voltage and dispensation of the specimen S to be successively performed.

FIGS. 5 to 12 illustrate variations of the voltage applier 2 of the analysis apparatus A. In these drawings, the constituents same as or similar to those of the foregoing embodiment are given the same numeral.

Figure 5:
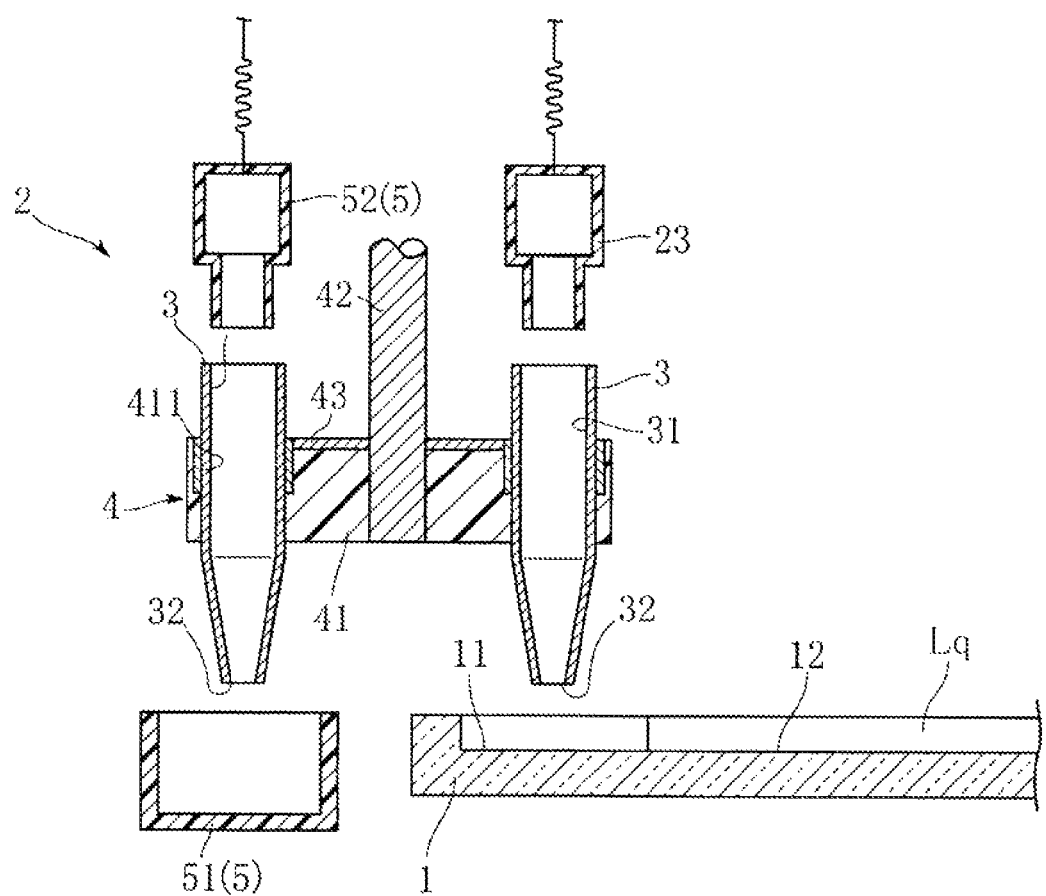
FIG. 5 is a fragmentary cross-sectional view showing a variation of a voltage applier with a cleaning mechanism.

FIG. 5 depicts a variation of the voltage applier of the analysis apparatus A. In this variation, the voltage applier 2 further includes a cleaning mechanism 5. The cleaning mechanism 5 includes a cleaning tank 51 and an injection nozzle 52. The cleaning tank 51 may be located, for example, right under the electrode 3 opposing the one located right above the introduction tank 11 of the microchip 1, with the rotary shaft 42 therebetween. The injection nozzle 52 is located further above the electrode 3 located right above the cleaning tank 51, and connected to a cleaning liquid tank (not shown) containing a cleaning liquid such as the electrophoretic liquid Lq.

Figure 6:
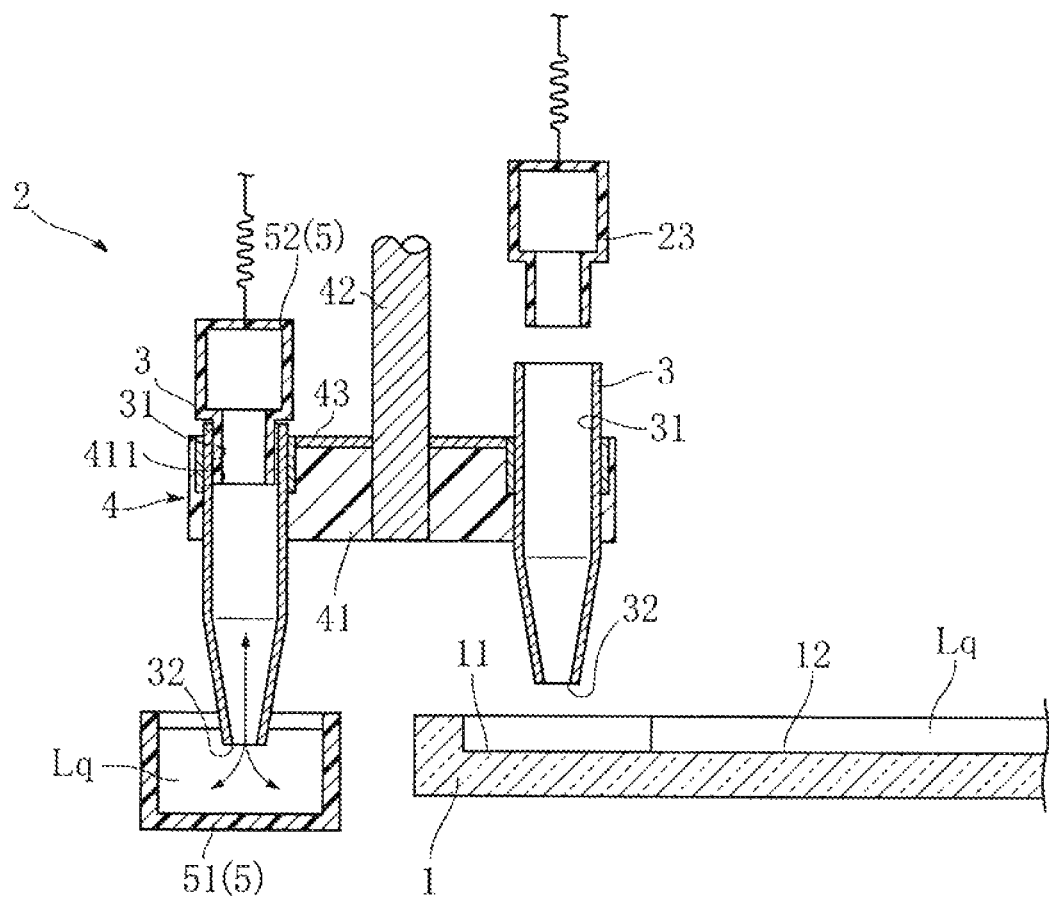
FIG. 6 is a fragmentary cross-sectional view for explaining a cleaning process of an electrode.

FIG. 6 depicts a cleaning operation performed by the cleaning mechanism 5. As shown therein, an actuator (now shown) like the actuator 25 causes the injection nozzle 52 to descend toward the electrode 3, so as to make the electrode 3 intrude into the cleaning tank 51. Then the electrophoretic liquid Lq, in this case serving as the cleaning liquid, is injected into the cleaning tank 51 through the injection nozzle 52 and the electrode 3. After introducing a predetermined amount of electrophoretic liquid Lq into the cleaning tank 51, the electrophoretic liquid Lq is discharged from the cleaning tank 51 through the electrode 3 and the injection nozzle 52. The injecting and discharging operations are performed, for example, by a pump which is not shown.

Such a mechanism allows the specimen S stuck to the electrode 3 and components of the electrophoretic liquid Lq deposited thereon to be removed by repeating the injection and discharging operations. Therefore, the cleaning mechanism allows the electrode 3 once used for the analysis to be used for a subsequent analysis, thereby further improving the efficiency of the analysis process.

The cleaning mechanism according to the present invention may employ a voltage applier, instead of the foregoing mechanism. For example, the components of the electrophoretic liquid Lq or specimen S may be deposited on the surface of the electrode 3 after voltage applications through a plurality of analysis processes. In this case, a voltage of a reverse polarity is applied to the electrode 3, with the electrode 3 soaked in the electrophoretic liquid Lq loaded in the cleaning tank 51. As a result, the substance deposited on the electrode 3 can be removed by electrolysis. Alternatively, a voltage significantly higher than the voltage for the analysis may be applied to the electrode 3 in the air. Such a method causes the substance deposited on the electrode 3 to be decomposed or burnt, thus to be removed.

Figure 7:
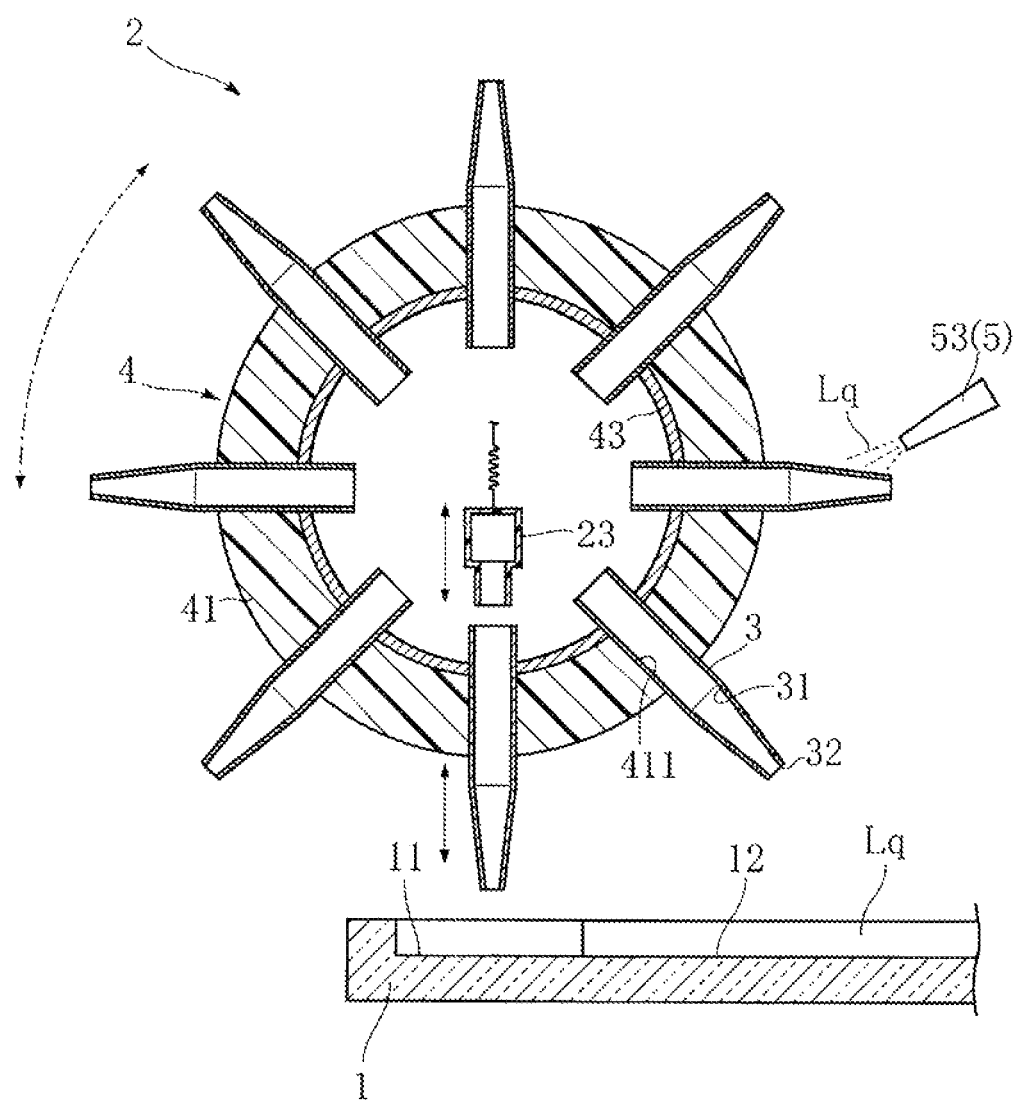
FIG. 7 is a fragmentary cross-sectional view showing another variation of the voltage applier.

FIG. 7 depicts another variation of the voltage applier 2. This variation is different from the foregoing examples in the arrangement of the plurality of electrodes 3. As shown in FIG. 7, the plurality of retention orifices 411 is formed radially of the retention unit 4. Accordingly, the electrodes 3 are radially disposed upon being inserted in the respective retention orifice 411. Such an arrangement also allows an unused one of the electrodes 3 to be brought to a working position by rotating the retention unit 4 by a predetermined angle, thereby enabling an accurate analysis to be efficiently performed.

In this variation, the cleaning mechanism 5 includes a cleaning nozzle 53. The cleaning nozzle 53 injects a cleaning liquid such as the electrophoretic liquid Lq to one of the electrodes 3 other than the one located at the working position, under the control of the control unit 7. The cleaning mechanism 5 thus configured also allows a used electrode 3 to be renewed to an unused state.

Figure 8:
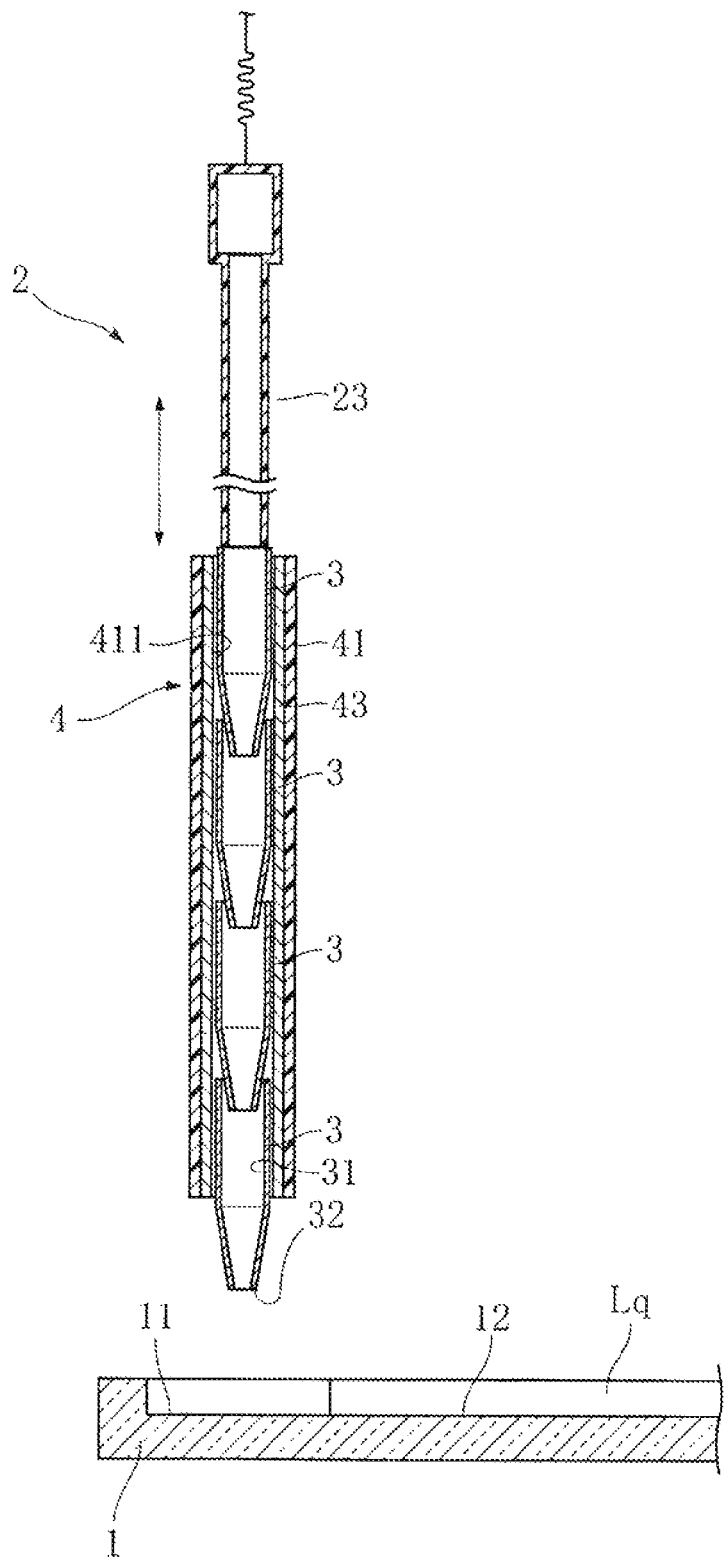
FIG. 8 is a fragmentary cross-sectional view showing still another variation of the voltage applier.

FIG. 8 depicts still another variation of the voltage applier 2. The voltage applier 2 according to this variation is different from the foregoing examples in the configuration of the retention unit 4 and retention method of the electrodes 3. As shown in FIG. 8, the retention unit 4 is formed in a lengthy cylindrical shape. The main body 41 has a cylindrical shape and includes therein the conductive portion 43. The plurality of electrodes 3 is serially aligned inside the retention unit 4, parallel to the longitudinal direction thereof. The electrodes 3 are slidably retained with respect to the retention unit 4. In this variation, a portion of the introduction nozzle 23 to be inserted in the retention orifice 411 of the retention unit 4 has substantially the same length as that of the retention unit 4. The introduction nozzle 23 is caused by the actuator 25 to gradually move downward by a predetermined distance.

Figure 9:
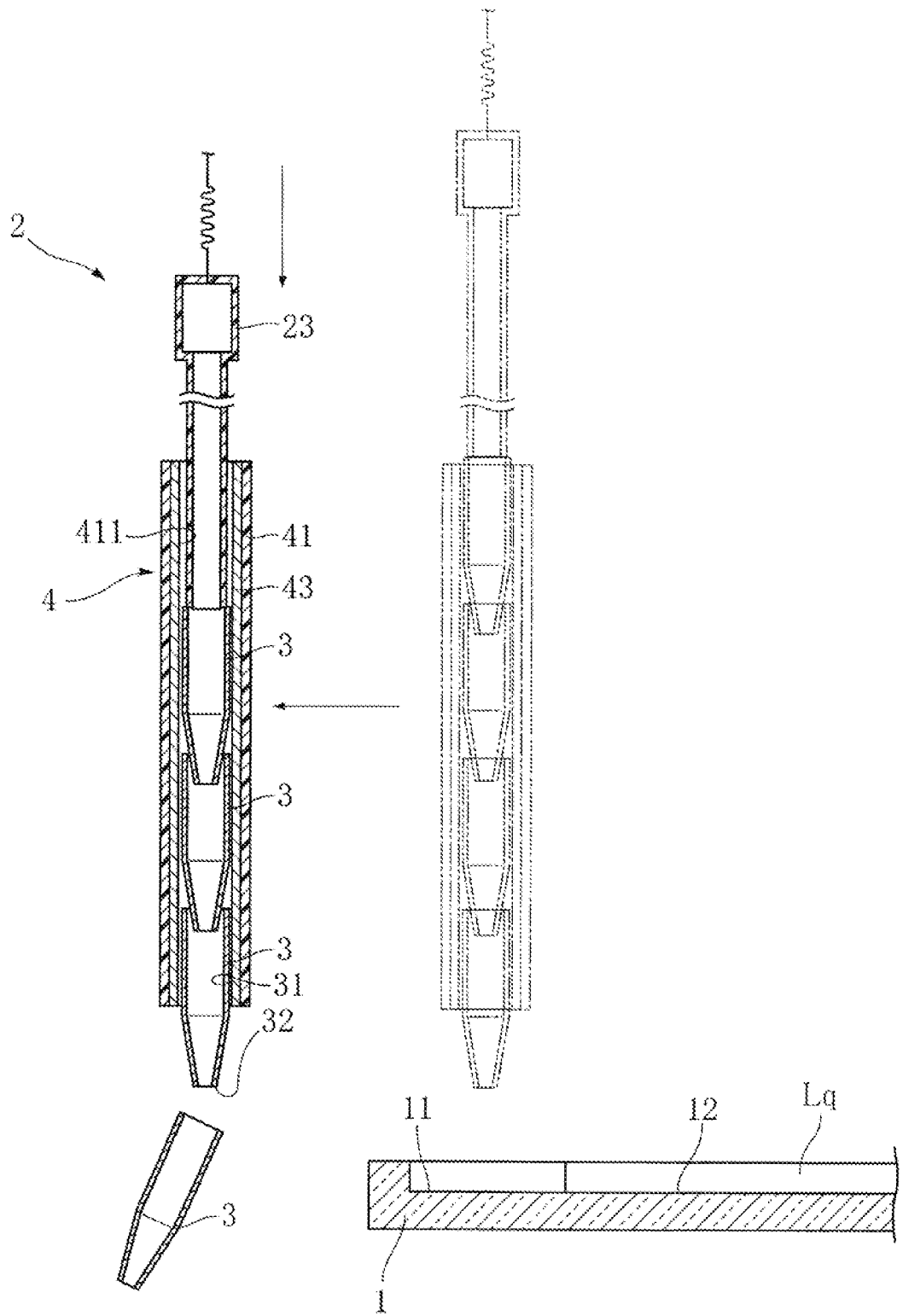
FIG. 9 is a fragmentary cross-sectional view for explaining replacement of the electrode in the variation shown in FIG. 8.

In the analysis process utilizing the voltage applier according to this variation, the lower end portion of a lowermost one of the electrodes 3 serves as the contact tip 32 to be soaked in the electrophoretic liquid Lq in the introduction tank 11. Upon completing an analysis process, the retention unit 4 is moved away to another position from right above the introduction tank 11, as shown in FIG. 9. Then the introduction nozzle 23 is caused to descend by the predetermined distance. As a result, the lowermost electrode is squeezed out from the retention unit 4, and the electrode 3 that has newly reached the lowermost position is used for a subsequent analysis process. Such an arrangement also enables a plurality of analysis processes to be accurately and efficiently performed.

Figure 10:
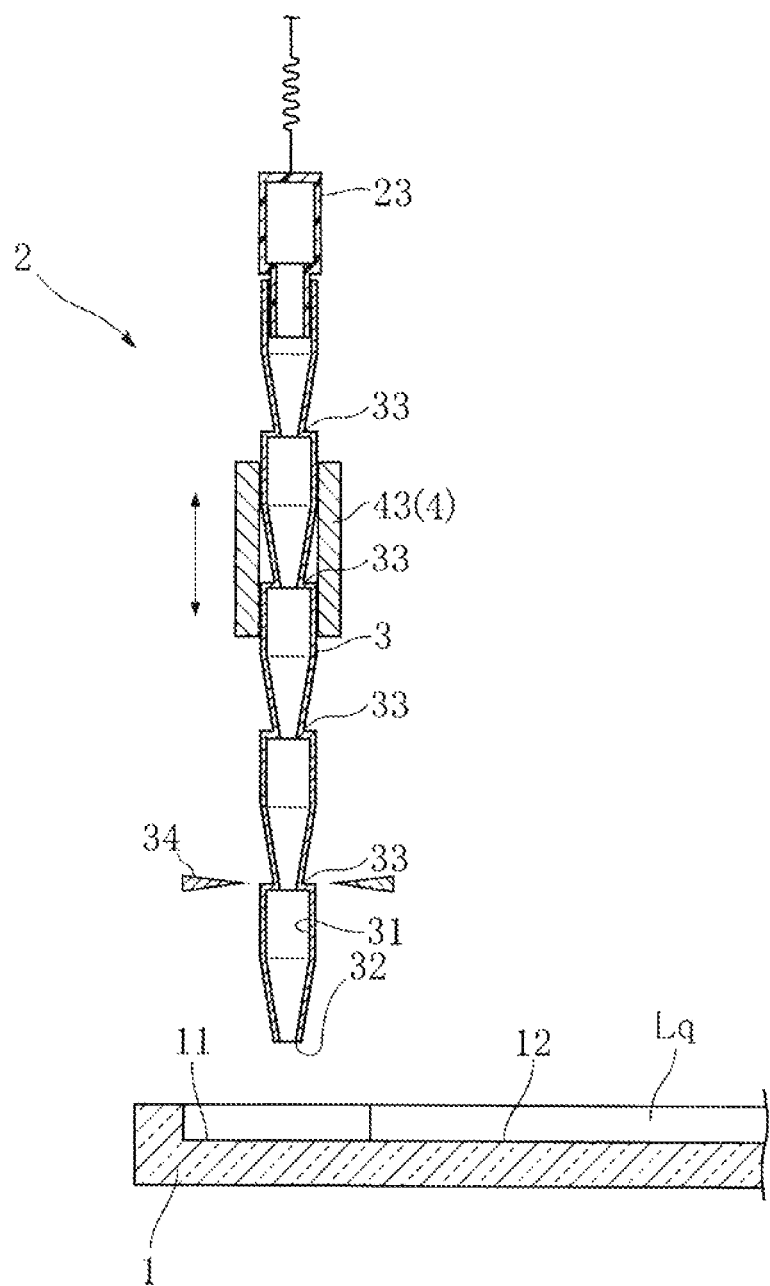
FIG. 10 is a fragmentary cross-sectional view showing still another variation of the voltage applier.

FIG. 10 depicts still another variation of the voltage applier 2. The voltage applier 2 according to this variation is different from the foregoing examples in the configuration of the electrode 3. The voltage applier 2 shown in FIG. 10 includes a single piece of electrode 3. This electrode 3 is relatively long and includes a plurality of cut positions 33. The cut positions 33 are provided at regular intervals longitudinally of the electrode 3. Each of the cut positions 33 are narrowed such that the cross-sectional area thereof is smaller than the remaining portion. The retention unit 4 is configured to serve as the conductive portion 43 as a whole, and to move up and downward retaining the electrode 3. The voltage applier 2 according to this variation also includes a pair of cutting blades 34. The pair of cutting blades 34 exemplifies a cutter according to the present invention, and is set to cut the electrode 3 at a position corresponding to a lowermost one of the plurality of cut positions 33. The process of soaking the contact tip 32 of the electrode 3 in the introduction tank 11 and performing the dispensation and voltage application is performed in the same manner as the foregoing examples.

Figure 11:
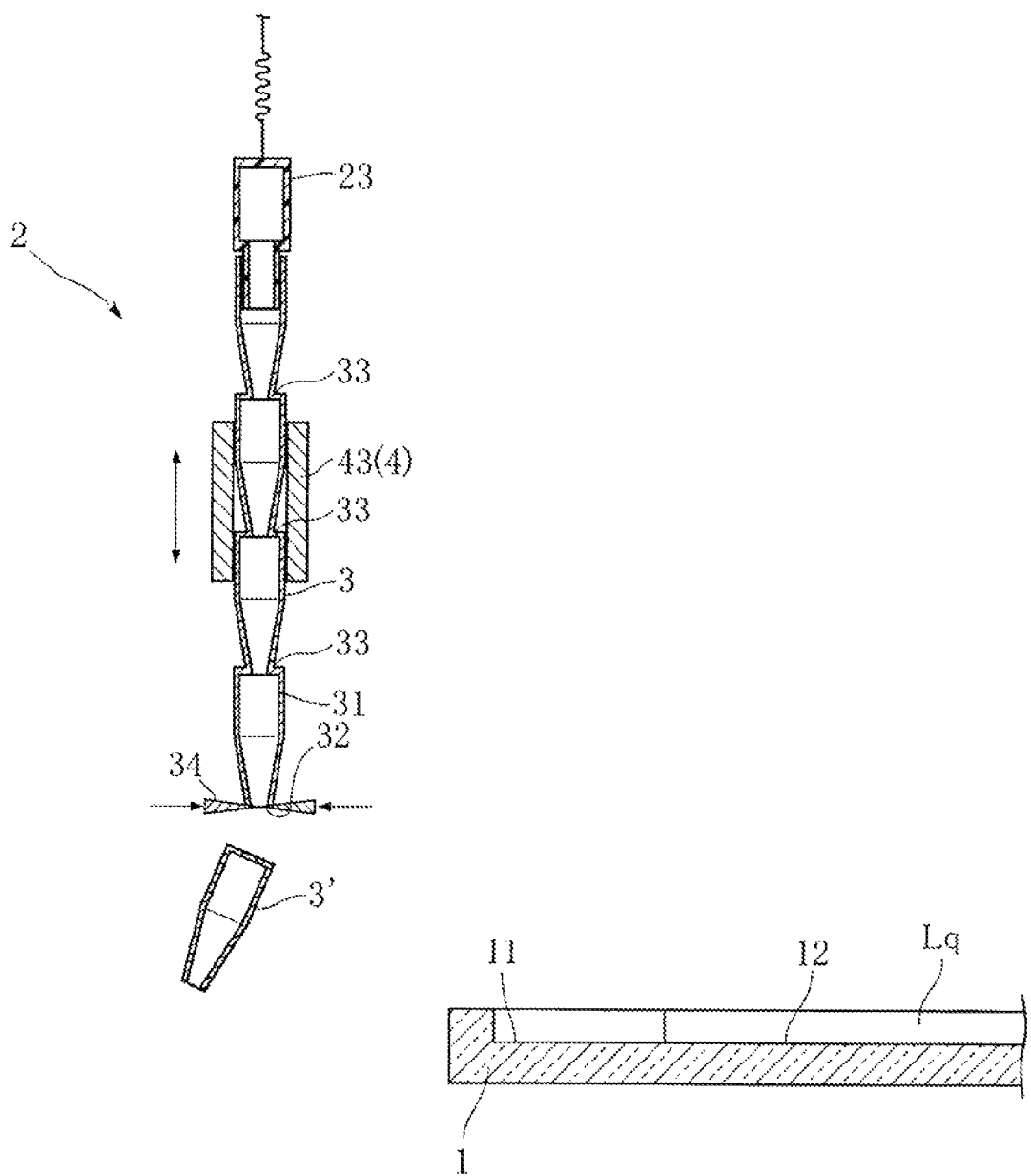
FIG. 11 is a fragmentary cross-sectional view showing a state where the electrode has been cut in the variation shown in FIG. 10.

Upon completing an analysis process, the retention unit 4 and the electrode 3 are moved away to another position from right above the introduction tank 11, as shown in FIG. 11. Then the pair of cutting blades 34 cuts the electrode 3 at the cut position 33, thereby removing the portion of the electrode 3 to which the specimen S has been stuck or on which the components of the electrophoretic liquid Lq have been deposited during the analysis. Thus, a portion of the electrode 3 that has newly reached the lowermost position is used as the contact tip 32 for a subsequent analysis process. Such an arrangement also enables a plurality of analysis processes to be accurately and efficiently performed.

Figure 12:
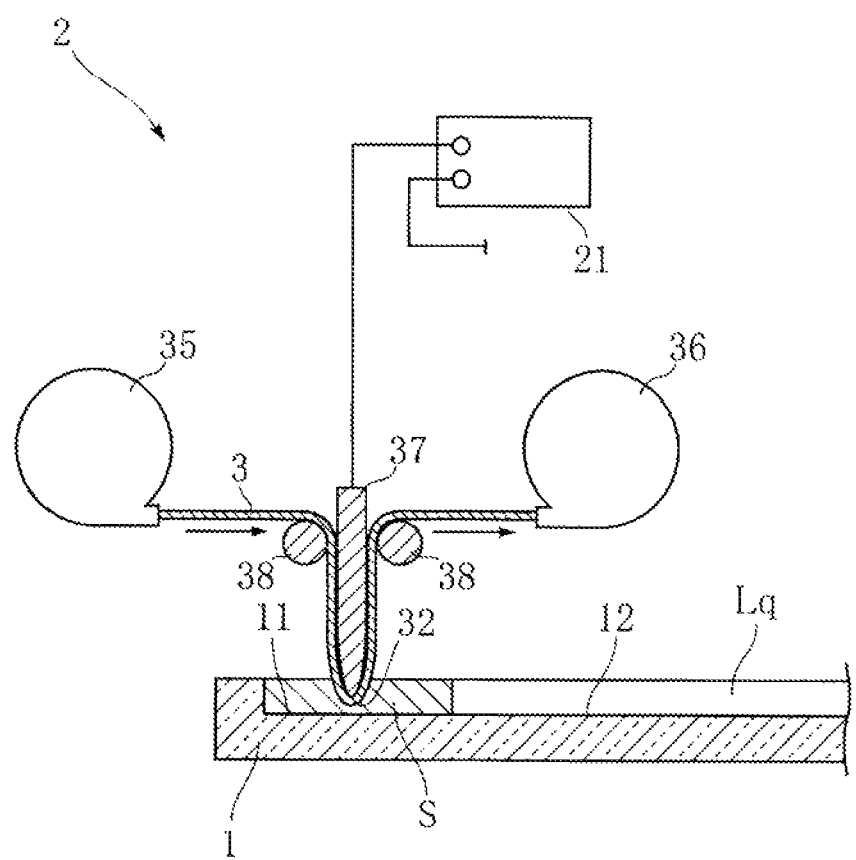
FIG. 12 is a fragmentary cross-sectional view showing still another variation of the voltage applier.
Figure 13:
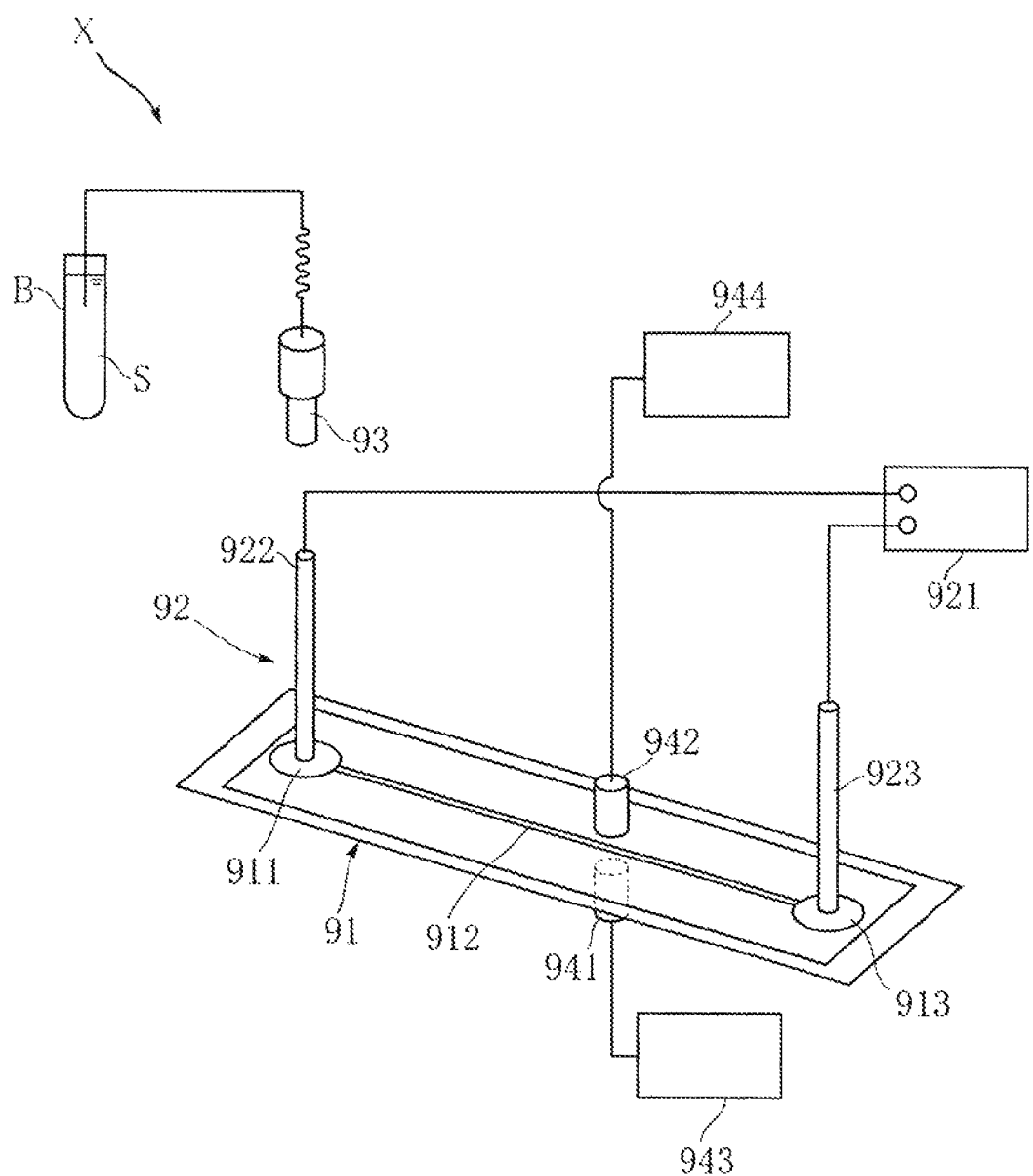
FIG. 13 is a schematic diagram showing an overall configuration of a conventional analysis apparatus.

FIG. 12 depicts still another variation of the voltage applier 2. The voltage applier 2 according to this variation includes a delivery wheel 35, a takeup wheel 36, a sticking bar 37, and a pair of rollers 38. In this variation, the electrode 3 is formed in a lengthy tape shape with a flexible nature. The delivery wheel 35 retains the electrode 3 wound thereon, and is configured to deliver the electrode 3. The takeup wheel 36 serves to take up the electrode 3 delivered from the delivery wheel 35, and for example includes a motor (not shown). The motor causes the takeup wheel 36 to take up the electrode 3 by a predetermined length, under the control of the control unit 7.

The sticking bar 37 serves to cause the electrode 3 to detour through the introduction tank 11. More specifically, the sticking bar 37 sticks out in a direction generally orthogonal to the route of the electrode 3 proceeding from the delivery wheel 35 toward the takeup wheel 36, such that a tip portion of the sticking bar 37 can reach the introduction tank 11. The pair of rollers 38 is located on the respective sides of the sticking bar 37. The electrode 3 is first engaged on the upstream roller 38 and then on the downstream one, passing over the tip portion of the sticking bar 37 therebetween. Thus, a portion of the electrode 3 covering the tip portion of the sticking bar 37 acts as the contact tip 32.

Upon completing an analysis process, the motor causes the takeup wheel 36 to take up the electrode 3 by the predetermined length, under the control of the control unit 7. Accordingly, the portion of the electrode 3 that was covering the tip portion of the sticking bar 37 moves to the downstream side, and the tip portion of the sticking bar 37 is covered with another portion of the electrode 3. As a result, the contact tip 32 is renewed from a used state to an unused state. Such an arrangement also enables a plurality of analysis processes to be accurately and efficiently performed. This variation further eliminates the need to throw away or cut the electrode 3 for each analysis process, thereby allowing the contact tip 32 to be smoothly renewed.

The analysis apparatus according to the present invention is in no way limited to the foregoing embodiments. A specific structure of the constituents of analysis apparatus according to the present invention may be modified in various manners.

It is not mandatory that the electrode 3 serves as the dispenser nozzle, and the electrode 3 may only serve to apply a voltage. Although the analysis apparatus according to the present invention is suitable for use in a capillary electrophoresis process, the present invention is also applicable to various analysis apparatuses configured to apply a voltage to a liquid specimen.

The invention claimed is:

1. An analysis apparatus comprising:
a detention tank in which a liquid is stored; and
a voltage applier including a power source and a contact tip to be brought into contact with the liquid for applying a voltage necessary for analyzing the liquid;
wherein the voltage applier renews the contact tip from a used state to an unused state after completing an analysis and before starting a subsequent analysis,
wherein the voltage applier includes a plurality of electrodes and sequentially soaks each of the electrodes in the detention tank, so that a portion of said each of the electrodes soaked in the liquid is used as the contact tip,
wherein the voltage applier further includes a retention unit that retains the plurality of electrodes aligned thereon so as to form a circle concentric with a center of the retention unit, the retention unit being configured to rotate about the center.

2. The analysis apparatus according to claim 1, wherein the retention unit includes a conductive portion for electrical connection between the power source and each of the electrodes.

3. The analysis apparatus according to claim 1, wherein each of the electrodes has a bar shape, and is disposed such that a longitudinal axis thereof is parallel to a rotary shaft of the retention unit.

4. The analysis apparatus according to claim 1, wherein each of the electrodes has a bar shape, and is disposed such that a longitudinal axis thereof is oriented in a radial direction of the retention unit perpendicular to the rotary shaft.

5. The analysis apparatus according to claim 3, wherein each of the electrodes includes a through-hole longitudinally penetrating therethrough, and the voltage applier further includes an introduction nozzle for introducing the liquid through the through-hole.

6. The analysis apparatus according to claim 5, wherein the introduction nozzle is configured to cause each of the electrodes to move toward the detention tank.

7. The analysis apparatus according to claim 5, wherein the voltage applier further includes a cleaning mechanism that cleans one of the electrodes that is not in use as the contact tip.

8. The analysis apparatus according to claim 7, wherein the cleaning mechanism is configured to inject and discharge a cleaning liquid to and from said one of the electrodes to be cleaned.

9. The analysis apparatus according to claim 7, wherein the cleaning mechanism applies a voltage to said one of the electrodes to be cleaned.

10. The analysis apparatus according to claim 1, wherein the analysis is performed utilizing an electrophoresis process.

11. The analysis apparatus according to claim 10, wherein the detention tank receives a specimen to be subjected to the analysis.

12. An analysis apparatus comprising:
a detention tank in which a liquid is stored; and
a voltage applier including a power source and a contact tip to be brought into contact with the liquid for applying a voltage necessary for analyzing the liquid;
wherein the voltage applier renews the contact tip from a used state to an unused state after completing an analysis and before starting a subsequent analysis,
wherein the voltage applier includes a plurality of electrodes and sequentially soaks each of the electrodes in the detention tank, so that a portion of said each of the electrodes soaked in the liquid is used as the contact tip,
wherein each of the plurality of electrodes has a bar shape, and the voltage applier further includes a retention unit that slidably retains the plurality of electrodes serially aligned in a longitudinal direction thereof,
wherein the retention unit includes a conductive portion for electrical connection between the power source and each of the electrodes,
wherein each of the electrodes includes a through-hole longitudinally penetrating therethrough, and the voltage applier further includes an introduction nozzle for introducing the liquid through the through-hole.

13. An analysis apparatus comprising:
a detention tank in which a liquid is stored; and
a voltage applier including a power source and a contact tip to be brought into contact with the liquid for applying a voltage necessary for analyzing the liquid;
wherein the voltage applier renews the contact tip from a used state to an unused state after completing an analysis and before starting a subsequent analysis,
wherein the voltage applier includes a bar-shaped electrode, and a cutter that cuts the electrode so as to longitudinally divide the electrode.

14. The analysis apparatus according to claim 13, wherein the electrode includes a plurality of narrowed portions located at intervals and smaller in cross-sectional area orthogonal to the longitudinal direction, and the cutter cuts the electrode at the narrowed portion.

15. An analysis apparatus comprising:
   a detention tank in which a liquid is stored; and
   a voltage applier including a power source and a contact tip to be brought into contact with the liquid for applying a voltage necessary for analyzing the liquid;
   wherein the voltage applier renews the contact tip from a used state to an unused state after completing an analysis and before starting a subsequent analysis,
   wherein the voltage applier includes a tape-shaped electrode, a delivery wheel that delivers the electrode wound thereon, and a takeup wheel that takes up the electrode delivered from the delivery wheel, and the voltage applier utilizes a portion of the electrode soaked in the liquid as the contact tip.

16. The analysis apparatus according to claim 15, wherein the voltage applier further includes a sticking bar that causes a portion of the electrode located between the delivery wheel and the takeup wheel to detour through the detention tank.

17. The analysis apparatus according to claim 16, wherein the sticking bar is formed of a conductive material and connected to the power source.

* * * * *